United States Patent [19]

Obermeier et al.

[11] Patent Number: 4,639,333

[45] Date of Patent: Jan. 27, 1987

[54] PROCESS FOR CONVERTING PREPROINSULIN ANALOGS INTO INSULINS

[75] Inventors: Rainer Obermeier, Hattersheim am Main; Rolf Geiger, Frankfurt am Main; Ulrich Grau, Hofheim am Taunus, all of Fed. Rep. of Germany

[73] Assignee: Hoechst Aktiengesellschaft, Fed. Rep. of Germany

[21] Appl. No.: 659,865

[22] Filed: Oct. 12, 1984

Related U.S. Application Data

[63] Continuation of Ser. No. 474,458, Mar. 11, 1983.

[30] Foreign Application Priority Data

Mar. 13, 1982 [DE] Fed. Rep. of Germany ....... 3209184

[51] Int. Cl.$^4$ .............................................. C07K 7/40
[52] U.S. Cl. ..................................... 530/303; 530/305
[58] Field of Search ..................................... 260/112.7

[56] References Cited

FOREIGN PATENT DOCUMENTS 2069502 8/1981 United Kingdom ............. 260/112.7

OTHER PUBLICATIONS

Roberts and Caserio, Basic Principles of Organic Chemistry, pp. 715–716.
Lehninger, Biochemistry, pp. 158–159.

*Primary Examiner*—Frederick E. Waddell
*Attorney, Agent, or Firm*—Finnegan, Henderson, Farabow, Garrett & Dunner

[57] ABSTRACT

The invention relates to a process for the preparation of insulins from analogs of preproinsulins, which comprises reacting preproinsulin analogs, at a pH below the isoelectric point of the insulins in the presence of trypsin or a trypsin-like endopeptidase, with an ester of natural amino acids or their derivatives and then cleaving off the ester group and other protective groups which may optionally be present.

16 Claims, No Drawings

PROCESS FOR CONVERTING PREPROINSULIN ANALOGS INTO INSULINS

This application is a continuation of application Ser. No. 474,458, filed Mar. 11, 1983, abandoned.

The invention relates to a process for the preparation of insulins from analogs of preproinsulins which comprises reacting preproinsulin analogs, at a pH below the isoelectric point of the insulins, in the presence of trypsin or a trypsin-like endopeptidase, with an ester of natural amino acids or derivatives of such an ester and then cleaving off the ester group and other protective groups which may optionally be present.

Pig insulin can be converted by various processes using enzyme-catalysed transamidation known per se (see, for example, German Offenlegungsschrift No. 31 04 949 and Obermeier R., et al., Proceedings Neue Insuline, Freiburg, 1981, in the press). In addition, these one-step processes are also suitable for generating insulin from proinsulin and intermediate insulins. Using trypsin in the conversion of pig insulin, under certain conditions according to the process, transamidation from $Lys^{B29}$-$Ala^{B30}$OH to $Lys^{B29}$-Thr-O-ester takes place, from which free insulin is prepared by known methods of ester cleavage. In the case of proinsulin or intermediate insulins, transamidation takes place from $Lys^{B29}$-$Ala^{B30}$-Arg.-Arg to $Lys^{B29}$-Thr-O-ester and also on Lys-$Arg^{A0}$-$Gly^{A1}$-.

The insulin formed in the human or animal body initially results in the form of a linear preproinsulin, the N-terminal $Phe^{B1}$-linkage presequence being constructed of about 24 amino acid residues. The function attributed to this part of the molecule is a signal action both for protein biosynthesis and also for the mechanism of transport through the membrane of the synthesizing cell.

The abovementioned semisynthetic preparation of human insulin from natural pig insulin is being displaced to an increasing extent by the production of human insulin as a chimeric gene product of modified E. coli DNA.

These genetic engineering methods permit the production of a product analogous to the natural preproinsulin by varying the signal nucleotide part. The aim of such changes in the amino acid sequence is the biosynthesis of an analogous preproinsulin which permits optimal cleavage to give insulin. In a known process (Riggs A. D., et al. Peptides 1979, ed. E. Gross and J. Meienhofer Pierce Chemical Company, Rockford, Ill., Pages 985–992), the presequence is modified such that it is linked via a methionine residue to the N-terminal $Phe^{B1}$ of the proinsulin, so that the Met-$Phe^{B1}$-bond can be cleaved using the BrCN method (Gross E., Witkop B., J. Bio. Chem. 1856 (1962)). The resulting proinsulin is then converted enzymatically (Kemmler A., J. Bio. Chem. 246, 3786 (1971)) with trypsin and carboxypeptidase B into human insulin. Both the BrCN cleavage and the treatment with the enzyme mixture, which follows in the second step, can cause considerable losses of final product due to non-specific reactions. Thus it is desirable to develop processes for producing insulin in high yields, that is to say with the smallest possible number of reaction steps, from analogous preproinsulins produced by genetic engineering.

This object is achieved by a process for the preparation of insulin from analogs of preproinsulin, which comprises carrying out simultaneously transamidation at the N-terminal peptide bond of $Phe^{B1}$ and $Gly^{A1}$ and at $Lys^{B29}$ of appropriate preproinsulins in the presence of the desired amino acid ester using trypsin or trypsin-like enzymes.

Analogous preproinsulins are those which have, at the N-terminal of the proinsulin, lysine or arginine or their acylaminoacyl radicals as the carboxyl end of a presequence (see formula I),

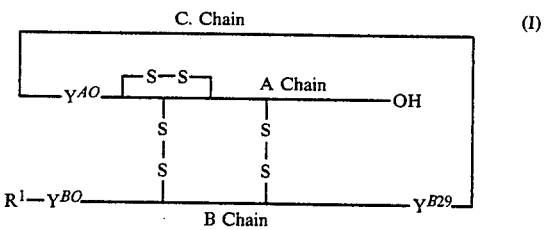

in which Y denotes Lys or Arg and $R^1$ denotes hydrogen, a L-amino acid or one of the peptide residues X described below.

X can be any peptide serving as a signal sequence. Any product which is coded for by a proinsulin gene, which is natural or has been altered synthetically by known processes of nucleotide variation, is suitable as the proinsulin part. Analogous preproinsulins having a shortened C-peptide segment, as is, for example, the case for the bovine C-peptide compared to the porcine C-peptide, are also suitable for the process. Likewise, human preproinsulin analogs are suitable. It is essential for the structure of the C-peptide that it is linked with the glycine of the insulin A chain via a basic L-amino acid Y=L-Arg or L-Lys; that is to say a structure Y-$(AA)_n$-Y is present, AA denoting all codeable amino acids and n being 0–35. Amino acid esters and/or their derivatives having free amino groups can also be selected for the process such that, if desired, an insulin analog not having a natural sequence is produced.

Esters or derivatives of esters of terminal amino acids in position B 30 of naturally occurring insulins are preferred. Most preferred are $(C_1$–$C_6)$-alkyl esters (eg. tert-butyl esters) and $(C_7$–$C_{19})$aralkyl esters (e.g. benzyhydryl, trityl or fluorenyl esters), in particular Ala-OtBu and Thr(+Bu)OtBu. Examples of suitable L-threonine esters are the tert.-butyl ester of L-threonine, the tert.-butyl ester of tert.-butyl-O-L-threonine and the methyl ester of L-threonine. Those derivatives of threonine esters having free amino groups in the context of the invention are to be understood as those which have a protective group, in particular an ether protective group, on the OH function of the threonine. Most preferred ether protective groups are $(C_1$–$C_6)$-alkyl, in particular tert.-butyl and $(C_7$–$C_{19})$-aralkyl, in particular benzhydryl, trityl or fluorenyl.

The optionally protected amino acid ester or its derivative having a free amino group is employed in a 50 to 500 molar ratio to insulin, preferably in the molar ratio of 100 to 250. The reaction is carried out at a pH below 5.5., preferably between pH 3.8 and 5.0, at a temperature between +2° and +37° C., preferably +4° and +10° C.

Apart from trypsin (c.f. "The Enzymes", Vol. 4, P. D. Boyer et al., Eds. Acad. Press, N.Y., 2nd ed. 1960, pp. 119–132; ibid. (3rd ed., 1971, pp. 250–275), those endopeptidases which are known from the literature as "trypsin-like", that is to say those which specifically cleave peptide bonds at the carboxyl end of basic amino acids, are suitable for the process according to the invention (c.f., for example "Kontakte Merck" 1/73 pp. 8-10, 2/73 pp. 3-8; Z. Physiol. Chem. 348 [1967] 1319; Comp. Biochem. Physiol. 28 [1969] 1275; Z. Physiol. Chem. 352 [1971] 583; Arch. Biochem. Biophys. 129 [1969] 620; ibid. 126 [1968] 971; Biochem. Biophys. Res. Comm. 37 [1969] 99). The amount of the enzyme to be used can be between 1:1 and 100:1, the figures relating to the ratio of weight of preproinsulin and analog:enzyme. A weight ratio of 10:1 to 4:1 is advantageously used.

The reaction according to the invention initially leads to B30 esters which may contain protective groups of the insulins, and these can be converted, if desired, by processes known per se by cleaving the ester group and, if necessary, cleaving off the protective group into the corresponding free insulin.

Before being converted into the free insulins, the esters can be subjected to the necessary purification operations, for example using known methods of column chromatography.

The insulin obtained can be used, formulated in customary forms for administration, as a medicament for treating diabetes mellitus.

The preproinsulin used in the Examples which follow were essentially obtained by known processes (Naithani V. K., et al., Insulins, ed. D. Brandenburg, A. Wolimer, 1980, W. de Gruyter, Berlin-New York, Pages 99-106) by direct acylation of proinsulin with the mixed anhydrides of BOC-Lys-(BOC)OH; BOC-Arg-(AdOC)$_2$-OH, BOC-Ala-Gln-Lys(BOC)OH, BOC-Ala-Gln-Arg(AdOC)$_2$-OH, BOC-Gln(tBu)-Pro-Lys(BOC)-Pro-Ala-Arg(AdOC)$_2$-OH and BOC-Gln(tBu)-Pro-Lys(BOC)-Pro-Ala-Lys(BOC)-OH. The compounds were purified over ion exchangers, and the protective groups were cleaved off with trifluoroacetic acid. Each amino acid analysis corresponded to the theoretical value.

EXAMPLE 1

(a) 75 mg of bovine Lys$^{B0}$-proinsulin, together with 250 mg of Ala-O(tBU), are dissolved in 0.5 ml of water and the pH is adjusted to 4.8 with a glacial acetic acid. 8 mg of trypsin, dissolved in 0.1 ml of water, is added to the solution. After standing at 4° C. for 16 hours, the reaction is stopped by precipitation with 68 ml of acetone. The precipitate is centrifuged off. After washing with ether, it is dried in vacuo.

This crude material is chromatographed over a silica gel column using the mobile phase chloroform/methanol/H$_2$O/triethylamine/formic acid=600/500/120/15/3. The first peak eluted is collected and evaporated to a small volume in vacuo. 25 ml of acetone are added to the solution and the precipitated bovine insulin B30-ester is centrifuged off. The precipitate is washed with ether and dried in vacuo.

Yield of bovine insulin B30-tBu: 41 mg.

(b) 25 mg of the bovine insulin B30-ester are dissolved in trifluoroacetic acid (0.5 ml) and allowed to stand at room temperature for 60 minutes. Then 5 ml of ether are added and the precipitated free bovine insulin is centrifuged off and, after washing with ether, dried in vacuo.

Yield: 23 mg.

Amino acid analysis, HPLC elution time and biological activity show values identical to bovine insulin.

EXAMPLE 2: (COMPARATIVE EXAMPLE)

500 mg of bovine LysB0-insulin (Geiger R., Chemiker-Zeitung 100, 111 (1976) and Geiger, R., Molecular Endocrinology, ed. Mac Intyre & Selke 1977, Elsevier/North Holland Biomedical Press, Pages 27-41), together with 2 g of Ala-O(tBu), are dissolved in 3.0 ml of water. The pH is adjusted to 4.5 with acetic acid. 20 mg of trypsin dissolved in 0.5 ml of water are added to the insulin solution. The process is continued in analogy to Example 1a. The yield of crude material, which contains 67% of bovine insulin B30-Ala-O(tBu) by HPLC analysis, is 563 mg.

The yield after purification by column chromatography is 409 mg.

The ester is cleaved off in analogy to Example 1b.

EXAMPLE 3

75 mg of bovine Ala-Gln-Lys$^{B0}$-proinsulin (for preparation see Example 1) are reacted in analogy to Example 1, but at +70° C. and pH 4.5, with trypsin and Ala-OtBU. After standing for 16 hours, the mixture is worked up and the bovine insulin B30-ester produced is separated off by chromatography.

Yield: 47 mg.

Amino acid analysis for this material corresponds to that of bovine insulin.

The ester is cleaved off in analogy to Example 1b.

EXAMPLE 4

75 mg of porcine Ala-Gln-Lys$^{B0}$-proinsulin (prepared in analogy to Example 3) are reacted, at +9° C. and pH 4.4, in analogy to Example 3 with Ala-OtBu and worked up. The yield of porcine insulin ester is 39 mg (working up in analogy to Example 1b).

EXAMPLE 5

75 mg of porcine Ala-Gln-Lys$^{B0}$-proinsulin are reacted with 500 mg of Thr(tBu)OtBu in the presence of trypsin as in Example 1a. After a reaction time of 16 hours, 49 mg of human insulin B30-(tBu)-OtBu can be isolated. The process is continued in analogy to Example 1b.

EXAMPLE 6

75 mg of bovine Arg-$^{B0}$-proinsulin are reacted with 500 mg of Thr(tBu)OtBu in the presence of trypsin as in Example 1a. After standing overnight, working up is as in Example 1a. The yield of bovine insulin B30-Thr(tBu)OtBu is 45 mg, which is further processed in accordance with Example 1b.

EXAMPLE 7

75 mg of porcine Ala-Gln-Arg$^{B0}$-proinsulin are brought to reaction with 400 mg of Thr(tBu)OtBu in the presence of trypsin as in Example 1a. After 20 hours at 6° C., the yield of human insulin B30(tBu)OtBu is 39 mg. (Further processing in analogy to Example 1b).

EXAMPLE 8

5 mg of bovine Gln-Pro-Lys-Pro-Ala-Gln-Lys$^{B0}$-proinsulin, together with 15 mg of AlaOtBu, are dissolved in 0.1 ml of water. The pH is adjusted to 4 to 5 with a trace of glacial acetic acid, and 1 mg of trypsin is added and the reaction is maintained at 4° C. for 24 hours. 63% of bovine insulin B30-tBu is measured using HPLC, and this is further treated as in Example 1b.

EXAMPLE 9

5 mg of porcine Gln-Pro-Lys-Pro-Ala-Gln-Arg$^{B0}$-proinsulin are brought to reaction with 25 mg of Thr(tBu)OtBu as indicated in Example 8. After a reaction time of 24 hours, 71% of human insulin B30-(tBu)OtBu were found by HPLC analysis. The ester was isolated using preparative HPLC.

Yield: 2.8 mg.

After the customary cleavage off of the tert.-butyl protective groups, the product was identical with human insulin in the HPLC and according to amino acid analysis.

EXAMPLE 10

75 mg of porcine Pro-Ala-Ala-Lys$^{B0}$-proinsulin are reacted with 500 mg of Thr(tBu)OtBu in the presence of trypsin as in Example 1a. After a reaction time of 16 hours, 52 mg of human insulin B30-(tBu)-OtBu can be isolated. Further processing is in analogy to Example 1b.

We claim:

1. A process for the preparation of insulin from a synthetic analog of human, bovine or procine preproinsulin of the formula I

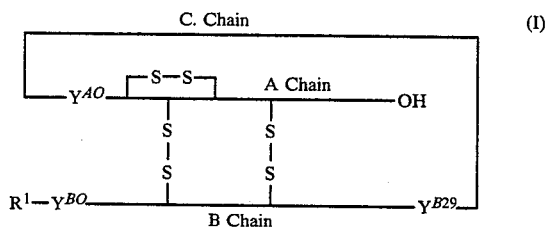

in which Y denotes Lys or Arg and R$^1$ denotes hydrogen, an L-amino acid or a peptide residue capable of serving as a signal sequence, which comprises reacting such preproinsulin analog, in a solvent system consisting of water and acetic acid at a pH below the isoelectric point of the insulin in the presence of trypsin or a trypsin-like endopeptidase, with an amino acid derivative selected from the group consisting of Ala-OtBu, Thr-OMe, Thr-OtBu and Thr(tBu)OtBu and then cleaving off the ester group and other protective groups which may be optionally present.

2. The process as claimed in claim 1, wherein said amino acid derivative is selected from the group consisting of Ala-OtBu and Thr(tBu)OtBu.

3. The process as claimed in claim 1, which is carried out at a pH between 3.8 and 5.5.

4. The process as claimed in claim 1, which is carried out at a pH between 3.8 and 5.0.

5. The process as claimed in claim 1, wherein the enzyme/substrate ratio is 1:1 to 1:100 parts by weight.

6. The process as claimed in claim 1, wherein the enzyme/substrate ratio is 1:4 to 1:10 parts by weight.

7. The process as claimed in claim 1, which is carried out in the presence of a 50 to 500-fold molar excess of said amino acid derivative.

8. The process as claimed in claim 1, which is carried out in the presence of a 100 to 250-fold molar excess of said amino acid derivative.

9. The process as claimed in claim 1, wherein the reaction temperature is between +2° and +37° C.

10. The process as claimed in claim 1, wherein the reaction temperature is between +4° and +10° C.

11. The process as claimed in claim 1, which is carried out at a pH between 3.8 and 5.5, the enzyme/substrate ratio being 1:1 to 1:100 parts by weight, a 50 to 500-fold molar excess of said amino acid derivative being used and the reaction temperature being between +2° and +37° C.

12. The process as claimed in claim 1, which is carried out at a pH between 3.8 and 5.0, the enzyme/substrate ratio being 1:4 to 1:10 parts by weight, a 100 to 250-fold molar excess of said amino acid derivative being used and the reaction temperature being between +4° and +10° C.

13. A process as claimed in claim 1 for the preparation of human insulin.

14. A process as claimed in claim 1 for the preparation of porcine insulin.

15. A process as claimed in claim 1 for the preparation of bovine insulin B30-ThrOH.

16. A Process as claimed in claim 13, wherein a preproinsulin analog is reacted with Thr(tBu)OtBu.

* * * * *